United States Patent
Tuma et al.

[11] Patent Number: 5,841,143
[45] Date of Patent: Nov. 24, 1998

[54] INTEGRATED FLUORESCENE

[75] Inventors: Margaret Tuma, Strongsville; Russell W. Gruhlke, Mt. Vernon, both of Ohio

[73] Assignee: The United States of America as represented by Administrator of the National Aeronautics and Space Administration, Washington, D.C.

[21] Appl. No.: 903,184

[22] Filed: Jul. 11, 1997

[51] Int. Cl.[6] .................................................. G01N 21/64
[52] U.S. Cl. ................................. 250/458.1; 250/459.1
[58] Field of Search ........................... 250/458.1, 459.1; 385/12, 37, 129, 130, 131

[56] References Cited

U.S. PATENT DOCUMENTS

| | | |
|---|---|---|
| 4,649,280 | 3/1987 | Holland . |
| 4,882,288 | 11/1989 | North et al. .......................... 250/461.1 |
| 5,006,716 | 4/1991 | Hall . |
| 5,449,918 | 9/1995 | Krull et al. .......................... 250/458.1 |

OTHER PUBLICATIONS

D. Hall and R. Gruhlke, Physical Review Letters, vol 56, p. 2838 (1986).

*Primary Examiner*—Edward J. Glick
*Assistant Examiner*—Darren M. Jiron
*Attorney, Agent, or Firm*—Kent N. Stone

[57] ABSTRACT

A detection method is integrated with a filtering method and an enhancement method to create a fluorescence sensor (10) that can be miniaturized. The fluorescence sensor (10) comprises a thin film geometry including a waveguide layer (16), a metal film layer (20) and sensor layer (32). The thin film geometry of the fluorescence sensor allows the detection of fluorescent radiation over a narrow wavelength interval. This enables wavelength discrimination and eliminates the detection of unwanted light from unknown or spurious sources.

31 Claims, 1 Drawing Sheet

INTEGRATED FLUORESCENE

ORIGIN OF THE INVENTION

The invention described herein was made by an example of the United States Government and by an employee of a contractor in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

This invention relates to the detection of fluorescence from molecules or atoms in a liquid, solid or gaseous sample. Specifically, this invention relates to a system and method for enhancing, filtering and sensing fluorescence from said molecules or atoms.

BACKGROUND ART

Fluorescence sensor systems typically employ optical detectors to detect the light emitted from a fluorescing substance. When light of a wavelength known to excite the fluorescent component of a particular substance is incident upon an unknown sample, the presence or absence of the substance in the sample may be indicated by detecting the presence or absence of a fluorescent emission. It is well known in the art that the excitation and emission wavelengths of a fluorescent material are different.

The reliability of a fluorescence sensor system is increased by increasing the intensity of the fluorescence emitted from the sample. U.S. Pat. No. 4,649,280 and 5,006,716 describe methods for increasing fluorescent intensity. The increase in the intensity of fluorescence emitted from a sample increases the sensitivity of the assay method. Thereby smaller quantities of fluorescent material in any given sample may be used for assay.

U.S. Pat. No. 4,649,280 by Holland, et al. describes a planar, thin metal and dielectric film structure on which the fluoresencing material is placed. This thin film structure supports the propagation of a variety of waveguide modes. Excitation radiation incident on the thin film structure couples to the waveguide modes. Such modes exhibit strong electromagnetic fields which envelope at least some of the fluoresencing material. The intensity of fluorescent emission, when a fluoresencing material is placed in close proximity to such a thin film structure, is increased relative to the intensity excited in a conventional system. Such a conventional system is defined as a fluorescent material placed on a glass microscope slide and subjected to incident excitation energy. A fluorescence intensity increase of 200 times that of such conventional systems is claimed by Holland.

A key problem with this method and that of other conventional methods is that the fluorescence emitted at a given wavelength is diffusely distributed about a normal to the flat surface of the fluorescent material. U.S. Pat. No. 5,006,716 by Hall is an improvement to the Holland method and describes a method which enables more efficient fluorescence collection. The Hall Patent describes a corrugated metal and dielectric thin film geometry that enables directional, enhanced fluorescent emission. Fluorescent radiation of a particular wavelength is emitted in a particular direction away from the fluorescing material. By placing an optical detector to intercept emitted light of a certain wavelength, a more efficient means of collection is achieved. A fluorescent intensity increase of 2,000 times that of conventional systems is claimed.

For the methods of fluorescence detection described in the Holland and Hall Patents, and for other conventional assay systems, the optical detector is removed from the fluorescing sample. The emission system is physically separated from the detection system. Detection and sample separation causes a number of problems. These include: 1) system geometries too large for miniaturization, and 2) the detection of unwanted light from spurious or unknown sources. In addition these prior art systems do not include any means of generating wavelengths of fluorescence in a selected wavelength range from fluorescing molecules located adjacent the prior art system.

Miniature optical detectors are currently fabricated using VLSI technology. Examples include semiconductor pn junctions used for optical interconnects and computer chips. These devices do not employ a method for the collection or emission of fluorescence and, therefore, can be considered only as components of a fluorescence sensor system. An example of a fluorescence sensor system containing a miniaturized component is a fiber optic based fluorescence sensor. The end of a fiber is a miniature receptor for the fluorescent radiation. This radiation is transmitted to a remote detector via the fiber.

With increasing detector separation from the source, the probability that light from unwanted sources will strike the detector is increased. Such sources increase the optical noise of detection and, thus decrease the signal to noise ratio. This is a major concern for fluorescence detection in hot environments, such as an airplane engine exhaust where black body radiation from hot regions may "wash out" the desired fluorescence signals. The detector placed at a distance from a fluorescence source can not discriminate non-fluorescent radiation, such as black body radiation, from fluorescent radiation having equal wavelength content. In the invention described in the Specification, only fluorescent radiation is transmitted to the sensing layer for detection. The sensing layer is shielded by a metal film from non-fluorescent radiation.

An additional problem with the prior art is that their systems and methods fail to discriminate between different wavelengths. Wavelength discrimination is important for samples containing multiple fluorescence sources. Each source is characterized by different emission spectrum. Reliable analysis of such samples requires wavelength discrimination. For the Holland Patent and other conventional fluorescence sensor systems, wavelength discrimination requires additional filtering components. Additional components increase costs and may introduce undesirable, thermomechanical properties, especially in hostile environments or configurations requiring miniaturization. By shielding the sensing material from all but a small wavelength range of radiation, the present invention described herein discriminates different wavelengths for detection. The median wavelength of this interval is determined by the thin film geometry design and can be easily varied.

The present invention integrates a sensing layer into a metal and dielectric film stack, thus solving many of the problems caused by the detector and source separation. Thin film geometry is easily miniaturized and transmission loss is reduced by the near proximity of source and sensor layer. A corrugated thin metal film is incorporated into the film geometry and prevents detection of unwanted light and enables wavelength discrimination.

The invention described herein physically integrates the detector into a thin film geometry emission system that constitutes a marked improvement from the system described in U.S. Pat. No. 5,006,716. The problems described for prior art separated detector/sample fluorescence sensor systems are eliminated. Therefore this invention is an improvement of the enhancement methods described in the Holland and Hall Patents. But more importantly this invention integrates a detection method with an enhancement method and a filtering method to create a new, thin film fluorescent sensor system that can be miniaturized.

DISCLOSURE OF THE INVENTION

An object of the present invention is to provide an integrated fluorescence enhancement, filtering and sensing system which integrates an optical sensor into a thin film geometry which includes the fluorescent sample to be detected.

A further object of the present invention is to provide an integrated fluorescence enhancement, filtering and sensing system which optimizes the signal to noise ratio reaching an optical sensor.

A further object of the present invention is to provide an integrated fluorescence enhancement, filtering and sensing system which can be used to analyze gas, liquid and solid materials, including high temperature materials.

A further object of the present invention is to provide an integrated fluorescence enhancement, filtering and sensing system which filters undesired fluorescence wavelengths from the optical sensor.

A further object of the present invention is to shield an integrated sensor from undesired sources emitting rediation of any wavelength.

A further object of the present invention is to provide an integrated fluorescence enhancement, filtering and sensing system which enhances florescence emitted from the sample material.

A further object of the present invention is to provide an integrated fluorescence enhancement, filtering and sensing system to convert fluorescent emissions into a corresponding electrical signal.

Further objects of the present invention will be made apparent from the following Best Modes for Carrying Out Invention and the appended Claims.

The foregoing objects are accomplished in the preferred embodiment of the invention by an article and method for analyzing fluorescence from a fluorescent material. The integrated fluorescence enhancement, filtering and sensing article of the present invention comprises an amount of fluorescent material in close proximity to a first surface of a dielectric waveguide layer. The waveguide layer is corrugated. The waveguide layer has a uniform thickness across parallel planes which extends parallel with the surface of a corrugated metal film layer. The corrugation of the waveguide layer and the metal film layer contains peak to valley distances of roughly 500 Angstroms and a periodicity equal to approximately one micron.

The waveguide layer supports optical excitations called waveguide modes for optical radiation at the wavelength of fluorescence and the wavelength of absorption of the fluorescent material. The electric field profile of these waveguide modes is evanescent. The waveguide modes penetrate into the fluorescent material and excite the fluorescence of the fluorescent material thereby enhancing the fluorescence of the fluorescent material.

At least one area of the metal film layer is corrugated and positioned adjacent to a second surface of the waveguide layer. The metal film layer is positioned in optical communication with the waveguide layer. The surfaces of the corrugated area of the metal film layer comprise a sinusoidal surface characterized by peak to valley distances of approximately 50 nanometers and by period distances of the order of one micron. The first surface of the waveguide layer is disposed from the second surface by the distance of several thousand Angstroms. The thickness of the metal film layer is approximately 500 Angstroms.

The metal film layer supports a first plurality of plasmons positioned on the interface of the metal film layer and the adjacent waveguide layer. Each of the first plurality of plasmons is excited at all fluorescent wavelengths, by radiative molecular decay and by waveguide modes within the waveguide layer, and produces a first plasmon field. The first plasmon field decays exponentially in amplitude with distance from the interface of the metal film layer and the adjacent waveguide layer. The metal film layer is thick enough as to be opaque to all light except that within a wavelength interval targeted for detection. The corrugated area admits all wavelengths of fluorescent energy through the metal film layer which are within the wavelength interval.

The article further comprises a sensor layer which is capable of absorbing optical energy from a plasmon field and generating a corresponding electrical signal. A dielectric buffer layer is interposed between the corrugated metal film and the sensor layer. The buffer layer is corrugated and has a uniform thickness across parallel planes which extends parallel with the surface of the metal film layer.

The metal film layer supports a second plurality of plasmons which are positioned at the interface between the dielectric buffer layer and the metal film layer. The second plurality of plasmons are positioned within the first plasmon field and are excited by the first plasmon field at a wavelength interval which includes the wavelength of fluorescence to produce a second plasmon field. The second plasmon field decays exponentially in amplitude with distance from the interface of the dielectric buffer layer and corrugated metal film.

The corrugated area on the metal film layer allows the coupling of the first plasmon field and the second plasmon field at a wavelength interval, which includes the wavelength of fluorescence of the fluorescent material. Thus the coupling of the plasmon fields creates a decay pathway for the fluorescence of molecules or atoms at the waveguide layer at the fluorescence wavelength.

The second plasmon field penetrates the sensor layer. The sensor layer comprises a corrugated surface positioned adjacent to the dielectric buffer layer. The sensor generates an electrical signal corresponding to the intensity of fluorescence of the fluorescent material at the wavelength of the fluorescence. In the preferred embodiment of the invention the sensor layer comprises a semiconductor pn junction. The semiconductor pn junction is positioned within the second plasmon field.

The method of detecting the fluorescence of the material comprises the steps of creating a sensor by depositing a thin film stack onto a sensing layer. The sensing layer comprises a corrugated surface and is operative to absorb the fluorescence and generate an electrical signal corresponding to the strength of the fluorescence. The thin film stack comprises a plurality of layers. The plurality of layers includes a layer of electrically conductive, opaque material disposed over the sensing layer. The electrically conductive layer comprises a plurality of plasmons on both surfaces. The plasmons operate to allow a decay pathway for the fluorescence of the material. The plurality of layers further includes a layer of dielectric material. The dielectric material layer is disposed over the electrically conductive layer. The layer of dielectric material supports waveguide modes for optical radiation at the wavelength of absorption by, and fluorescence from the material. The sensor layer, the electrically conductive layer and the dielectric layer all have parallel corrugated surfaces. Each of the corrugated surfaces can have sinusoidal corrugation profiles.

The method of detecting the fluorescence of a material further comprises the step of placing the sensor in close proximity with the material. Alternatively, a film of the material is deposited on a surface of the waveguide. When placed in close proximity with the material, the waveguide modes excite the material to fluoresce, whereby there is an enhanced fluorescence from the material. The waveguide modes are excited by incident light, such as light from a laser or from incident light of TM or TE polarization. Plasmons positioned on the surface of the electrically conductive layer adjacent the dielectric layer are excited by the waveguide modes, by incident light and by the fluorescing material.

The method of detecting the fluorescence of a material finally comprises the step of detecting the fluorescence of the material by monitoring the electrical signal from the sensing layer to determine the amount of fluorescence emanating from the material and passing through the waveguide to the sensing layer.

BRIEF DESCRIPTION OF DRAWING

A preferred embodiment of the invention and integrated florescence enhancement filtering sensing system and method is described herein in detail with reference to the accompanying drawing.

BEST MODES FOR CARRYING OUT INVENTION

Figure 1:
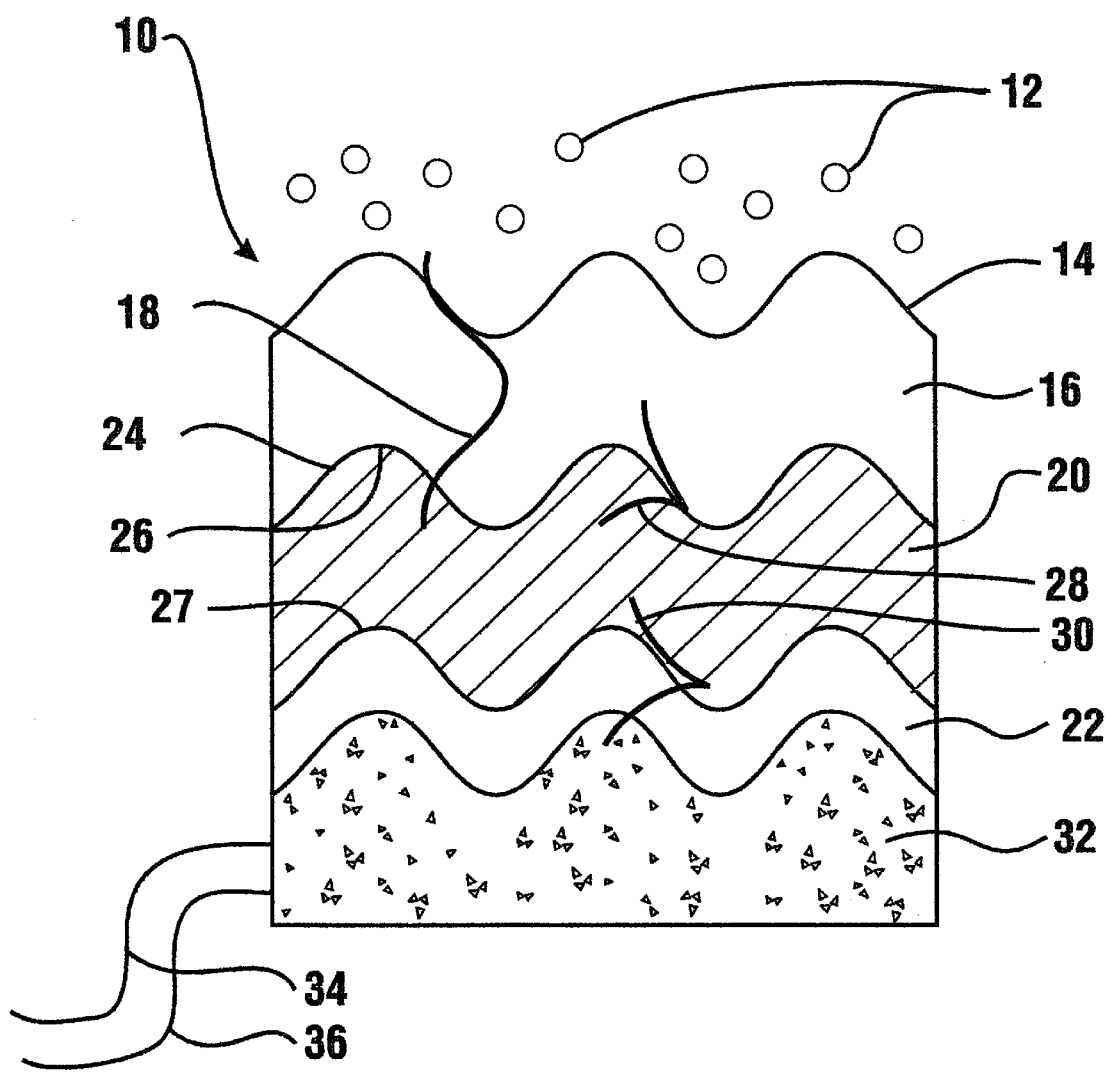
FIG. 1 is a cross sectional view of the stack of thin dielectric, metal and semiconductor films placed adjacent to some sample material of the present invention.

Referring now to the drawing, FIG. 1, the fluorescence sensor 10 of the present invention is shown. The fluorescence sensor 10 comprises a stack of thin films. A fluorescent material 12 is placed adjacent the fluorescence sensor. The material 12 may be in a gaseous, liquid or solid state. Alternatively, a film of the material 12 can be deposited on a first surface 14 of the fluorescence sensor. The topmost layer in the film stack of the fluorescence sensor is a dielectric waveguide layer 16. The waveguide layer supports a variety of waveguide modes. For purposes of the specification and claims, waveguide modes are defined as optical excitations confined to the waveguide layer. These waveguide modes have inherent electric and magnetic field profiles which decrease in amplitude with increasing distance from the waveguide layer. Waveguide mode field 18 superimposed over the waveguide layer 16 depicts a decreasing strength of the waveguide mode field as a function of distance from the center of the waveguide layer 16. Note a portion of the waveguide mode field 18 extends into the fluorescent material 12.

The waveguide layer 16 is deposited on an underlying metal film 20. The metal film 20 is sandwiched between the waveguide layer 16 and an underlying buffer layer 22. The waveguide layer 16 interfaces with the metal film 20 at a second surface 24. bossy waveguide modes called surface plasmons are supported at opposite metal to dielectric interfaces on both surfaces of the metal film 20. A first plurality of plasmons is supported at interface 26 of the waveguide layer 16 and the metal film 20 adjacent the second surface 24. A second plurality of plasmons is supported at interface 27 of the buffer layer 22 and the metal film 20. The surface plasmons are characterized by electric and magnetic fields, the amplitudes of which decay exponentially away from the metal to dielectric interface. The first plurality of plasmons produces a first field 28, the field strength of which is shown graphically decaying from the dielectric waveguide layer to metal film interface. Similarly the second plurality of plasmons produces a second field 30, the field strength of which is shown graphically decaying with distance away from the metal film to buffer layer interface.

The buffer layer 22 is composed of a dielectric material and separates the metal film 20 from a sensor layer 32. The sensing layer is composed of any material having electrical properties affected by the absorption of light. Preferable candidates are semiconductor pn or np junctions. In these materials light incident the junction, when absorbed, cause an electron transition in the conduction band. The application of a voltage sweeps out this current as a signal. Voltage or resistance changes may also be measured. To measure these electrical signals, electrical leads 34 and 36 are supplied in electrical communication with the sensor layer 32.

In the preferred embodiment of the invention, the sensing layer 32, the buffer layer 22, the metal film 20 and the waveguide layer 16 are all corrugated. Corrugation is fabricated directly into either the buffer layer 22 or the sensor layer 32. Corrugation is preferably a sinusoidal surface relief characterized by peak to valley distances of approximately 50 nanometers and by periodicity or pitch distances on the order of one micron. Fabrication of the corrugation is accomplished by first spinning a photoresist layer on the planar dielectric or sensing layer. The photoresist is then exposed to two interfering laser beams of the same wavelength. This causes a sinusoidal variation in the photoresist exposure. Upon development of the photoresist layer, the variation manifests as a sinusoidal surface relief. This pattern is transmitted into the dielectric or sensing layer by ion beam milling or dry chemical etching, also known as a reactive ion etching. Other means of achieving a surface profile in photoresist include exposure using a photolithographic tool.

When the corrugation is imported into the sensing layer, the dielectric layer can then be deposited onto the sensing layer by several different techniques. Dielectric material such as lithium fluoride or silicon nitride may be deposited by resistive or electron beam evaporation, ion beam or RF sputtering techniques. Polymer and photoresist layers may be deposited by spinning the material onto the underlying sensing layer. The dielectric buffer layer is thin enough, 50 to 100 nanometers, to allow penetration of the second plasmon fields into the sensor layer. In the preferred embodiment of the invention the waveguide layer and the buffer layer, positioned on either side of the metal film, are of different materials characterized by different refractive indices.

The metal film 20 is formed by the deposition of metal on the underlying buffer layer 22. This deposition can be accomplished by electron beam or resistive evaporation, ion beam or RF sputtering. The metal film is thin enough, approximately 50 nanometers, to conform to the surface relief of the underlying buffer layer 22.

The waveguide layer 16 can be deposited in the same manner as that of the buffer layer 22. Again, material such as lithium fluoride or silicon nitride may be deposited by resistive or electron beam evaporation, ion beam or RF sputtering techniques. Polymer and photoresist layers may be deposited by spinning the material onto the underlying layer. In all cases, the typical thickness of the waveguide layer is 200 to 300 nanometers.

The area of corrugation does not necessarily need to extend over the entire surface area of the thin film layers. The area of corrugation on the metal film layer acts as a grating which functions as a wavelength discriminator, the function of which is more fully described below. The dielectric and the sensor layers need not be corrugated and are corrugated for manufacturing purposes and to structurally support the corrugation of the metal film layer. The area of corrugation on the metal film layer may be any size. The metal film layer may be manufactured with multiple corrugation areas, each with dissimilar periodicities of corrugation. Each area with its characteristic periodicity acts to filter a corresponding wavelength of interest.

As described above, the fluorescence sensor operates to enhance the fluorescence of the fluorescent material 12, to filter unwanted optical wavelengths from reaching the sensing material, and senses the emitted fluorescence from the fluorescent material.

Atoms and molecules in the fluorescent material 12 are excited by absorption of incident excitation radiation. This light is incident to the fluorescent material from either an external source or from light confined to the dielectric waveguide layer via a waveguide mode. In either case, this radiation has a wavelength content known to excite atoms or molecules of interest in the fluorescent material 12. In general, wavelengths at which an atom or molecule is excited to emit florescence are different from the wavelengths characteristic of fluorescent emissions from that same atom or molecule. The fluorescence sensor 10 of the present invention enhances the light intensity of the fluorescent material 12 by employing the waveguide layer 16 to generate a strong electromagnetic field in the vicinity of the fluorescent material 12. The excitation energy, which is incident on the fluorescent material, is self coupled to the waveguide layer to support the propagation of the waveguide modes which generate the strong field. This combination causes more intense fluorescence relative to that excited by radiation incident on conventional systems, such as fluorescent material coated on a glass slide. The strong electromagnetic field generated by the waveguide modes is responsible for the increased fluorescence. The increase is a function of the dimensions of the waveguide layer which supports the waveguide modes. However, the intensity of the fluorescence can be increased nearly 200 times relative that of conventional systems.

A fluorescent radiative energy flows into the thin film stack of the fluorescence sensor 10 away from the fluorescent material 12. The wavelength content of the resulting waveguide modes is the same as that of the fluorescent emission spectra of the fluorescing atoms or molecules in the fluorescent material 12. The first and second plurality of plasmons act to create a decay pathway through the otherwise opaque metal film layer 20. The metal film layer acts to filter unwanted wavelengths from reaching the sensing material. The first plurality of plasmons generated at the dielectric waveguide layer and metal film interface are excited at all fluorescent emission wavelengths contained in the waveguide modes within the waveguide layer 16. The metal film layer 20 is thin enough so that the surface plasmon fields on opposite sides of the metal film overlap.

The presence of a corrugation area within the metal film layer 20 enables the momentum matching of surface plasmons having equal wavelengths but localized to opposite sides of the metal film layer. Over a narrow range of wavelengths, surface plasmon "cross-coupling" occurs and surface plasmons are generated on the metal film layer side opposite the fluorescent material, that is at the metal film 20 and buffer layer 22 interface. Thus over a small wavelength interval optical energy is transmitted across an otherwise opaque thin metal film via the first plurality of plasmons and second plurality of plasmons interactions. Thus at the desired wavelength of fluorescence, plasmons with identical momentum can be supported at both metal and dielectric interfaces. The metal film layer 20 is thin enough so that the first field 28 and the second field 30 overlap at the cross coupling wavelength of the fluorescent emitting wavelength and a single complicated plasmon mode having peak field amplitude at both interfaces is created. This mode "feels" both sides of the metal film and thus can transmit energy across the film. Only energy at the desired wavelength is transmitted, thus the single plasmon mode and the metal film act to filter unwanted wavelengths, i.e. noise, thus optimizing or maximizing the signal to noise ratio. Fluorescence intensities 2,000 times relative that of conventional systems are transmitted to the sensing layer.

The periodicity of the corrugation determines the wavelength at which the surface plasmons can cross couple and therefore also determines the admitted wavelength of fluorescence. The corrugation period needed for a desired wavelength can be calculated. The relationship between the corrugation period and the transmitted wavelength is more fully described in Physical Review Letters, Volume 56, page 2838 (1986) by Dennis Hall and Russell Gruhlke, the content of which is incorporated by reference herein. Corrugation areas with periodicities corresponding to desired wavelengths can be incorporated into the metal film layer. The relationship between the corrugation periodicity and the admitted wavelength is also affected by the index of refraction of the dielectric layers on both sides of the metal film layer. A nonlimiting example of the relationship between the corrugation periodicity, the dielectric properties and the admitted wavelength is as follows: in order to cross couple plasmons at a wavelength equal to 600 nm, a corrugated area with a 760 nm periodicity is required. The corrugated metal film layer was bounded in this example by a dielectric with an index of refraction, n=1.63 on one side with air on the other side.

The buffer layer 22 is thin enough to allow the penetration of the second plasmon field into the sensor layer 32. Alternatively, the buffer layer can be omitted from the sensor 10 and the sensor layer can be positioned adjacent the metal film 20.

As stated, the transmitted fluorescent energy transmitted across the metal film layer 20 is absorbed in the sensor layer 32. In the preferred embodiment of the invention the sensing layer is a semiconductor material containing a pn junction. In this embodiment the absorbed energy generates a conduction band electron. This affects the electrical properties of the sensing layer and can be measured as a current or change in resistance or voltage. This electrical signal denotes a fluorescent event occurring in the narrow wavelength range. Pn or np type semiconductor materials are formed by a doping process. This art is well known in the semiconductor industry. Atoms such as aluminum or boron are thermally diffused or ion implanted into the intrinsic material such as silicon. It is important that the pn or np junction fabricated within the sensing layer is located near the surface of the sensor layer within the range of the second field. The second field generated by the second plurality of plasmons can then penetrate the sensor layer to the pn or np junction.

Thus the invention achieves the above stated objectives, eliminates difficulties encountered in the use of prior devices, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations herein are by way of examples and the invention is not limited to the exact details shown and described.

Having described the features, discoveries and principles of the invention, the manner in which it is constructed and operated and the advantages and useful results attained; the new and useful structures, elements, arrangements, parts, combinations, systems, operations and relationships are set forth in the appended claims.

We claim:

1. An article for analyzing fluorescence from a fluorescent material comprising:

fluorescent material in close proximity to a first surface of a dielectric waveguide layer, wherein said waveguide layer supports waveguide modes at the wavelength of fluorescence and wavelength of absorption of said fluorescent material, wherein said waveguide modes penetrate into said fluorescent material and excite the fluorescence of said fluorescent material, whereby the fluorescence of said fluorescent material is enhanced;

a corrugated metal film layer positioned adjacent to a second surface of said waveguide layer, wherein said metal film layer supports a first plurality of plasmons positioned at the interface of said metal film layer and said adjacent waveguide layer, wherein each of said first plurality of plasmons is excited by all fluorescent wavelengths within said waveguide layer, and said first plurality of plasmons produces a first field, a sensor layer, wherein said sensor layer is capable of absorbing optical energy and generating a corresponding electrical signal, wherein said metal film layer supports a second plurality of plasmons, wherein said second plurality of plasmons is positioned within said first plasmon field and is excited by said first plasmon field at a wavelength interval which includes the wavelength of fluorescence to produce a second plasmon field, wherein said second plasmon field penetrates said sensor layer, whereby said sensor layer generates an electrical signal corresponding to the fluorescence intensity of the fluorescent material at the wavelength of fluorescence.

2. The article of claim 1, wherein said metal film layer is opaque to all wavelengths not within said wavelength interval.

3. The article of claim 1, further comprising a dielectric buffer layer, wherein said buffer layer is interposed between said sensor layer and said corrugated metal film layer.

4. The article of claim 3, wherein said second plurality of plasmons are positioned at the interface of said corrugated metal film layer and said buffer layer.

5. The article of claim 3, wherein said buffer layer has a uniform thickness across parallel planes which extend parallel with the surface of said metal film layer.

6. The article of claim 1, wherein said waveguide layer has a uniform thickness across parallel planes which extend parallel with the surface of said metal film layer.

7. The article of claim 1, wherein said sensor layer comprises a semiconductor pn junction, wherein said semiconductor pn junction is positioned within said second plasmon field.

8. The article of claim 1, wherein a first area of said metal film layer is corrugated at a first periodicity, wherein a second area of said metal film layer is corrugated at a second periodicity.

9. The article of claim 1, wherein each of the surfaces of said corrugated metal layer comprises a sinusoidal surface relief characterized by peak to valley distances of approximately 50 nanometers and by periodicity of the order of one micron.

10. An article for analyzing the fluorescence from a fluorescent material comprising:

a fluorescent material layer;

a dielectric layer;

a metal film layer positioned in optical communication with said dielectric layer, wherein said metal film layer supports a first plasmon, wherein said first plasmon produces a first field when excited by fluorescence from said fluorescent material layer, wherein said metal film layer supports a second plasmon, wherein said second plasmon is positioned within said first field and is excited by said first field at a wavelength interval which includes said wavelength of fluorescence to produce a second field, whereby a decay pathway for the fluorescence from said fluorescent material layer at said fluorescent wavelength is produced;

a sensor layer, wherein said second field penetrates said sensor layer, whereby said sensor layer absorbs optical energy from said second field and generates a signal corresponding to the fluorescence of the fluorescent material at the wavelength of fluorescence.

11. The article of claim 10, wherein said dielectric layer supports waveguide modes for optical radiation at said wavelength of fluorescence and wavelength of absorption of said fluorescent material, wherein said waveguide modes penetrate into said fluorescent material layer and excite the fluorescence of said fluorescent material, whereby the fluorescence of said fluorescent material is enhanced.

12. The article of claim 10, wherein a first area of said metal film layer is corrugated with a first periodicity, wherein said first area is transparent to all wavelengths within said wavelength interval.

13. The article of claim 12, wherein a second area of said metal film layer is corrugated with a second periodicity, wherein said second-area is transparent to all wavelengths within a second wavelength interval.

14. The article of claim 13, wherein said dielectric layer supports waveguide modes for optical radiation at said wavelength of fluorescence and wavelength of absorption of said fluorescent material, wherein said waveguide modes penetrate into said fluorescent material layer and excite the fluorescence of said fluorescent material, whereby the fluorescence of said fluorescent material is enhanced.

15. The article of claim 14, wherein said metal film layer is opaque to all wavelengths not within said wavelength interval, whereby the noise received by said sensor is reduced.

16. The article of claim 10, wherein said metal film layer is opaque to all wavelengths not within said wavelength interval, whereby the noise received by said sensor is reduced.

17. The article of claim 10, wherein said sensor layer comprises a semiconductor pn junction, wherein said semiconductor pn junction is positioned within said second field, and wherein said signal is electrical.

18. The article of claim 10, wherein said dielectric layer is bounded by said metal film layer and said fluorescent material layer, wherein said first plasmon is positioned at the interface of said dielectric layer and said metal film layer.

19. The article of claim 10, further comprising a buffer layer, wherein said buffer layer comprises a dielectric material, wherein said buffer layer is interposed between said sensor layer and said metal film layer, wherein said second plasmon is supported at the interface of said buffer layer and said metal film layer.

20. A method of detecting the fluorescence of a material comprising the steps of:
   creating a sensor by depositing a thin film stack onto a sensing layer, wherein said sensing layer is operative to absorb fluorescence and generate an electrical signal corresponding to the strength of said fluorescence, wherein said thin film stack comprises a plurality of layers, said plurality of layers including:
      a layer of electrically conductive, opaque material disposed over the sensing layer, comprising a plurality of plasmons on the surfaces of said layer, wherein said plasmons operate to allow a decay pathway for the fluorescence of said material,
      a layer of dielectric material disposed over said electrically conductive layer, wherein said layer of dielectric material supports waveguide modes for optical radiation at the wavelength of absorption by and fluorescence from said material;
   placing said sensor in close proximity with said material;
   detecting the fluorescence of said material by monitoring said electrical signal from said sensing layer to determine the amount of fluorescence emanating,. from said material and passing through said layer dielectric material to said sensing layer.

21. The method of claim 20 wherein said waveguide modes excite said material to fluoresce whereby there is enhanced fluorescence from said material.

22. The method of claim 20 wherein a film of said material is deposited on a surface of said waveguide.

23. The method of claim 20 further comprising the step of corrugating a first area of said electrically conductive layer with a first periodicity.

24. The method of claim 23 further comprising the step of corrugating a second area of said electrically conductive layer with a second periodicity.

25. The method of claim 20 wherein said sensor layer, said electrically conductive layer and said dielectric material layer all have parallel surfaces.

26. The method of claim 20 wherein said waveguide modes are excited by incident light.

27. The method of claim 26 wherein said incident light is from a laser.

28. The method of claim 20 wherein said waveguide modes are excited by incident light of TM or TE polarization.

29. The method of claim 20, wherein said sensor layer comprises a semiconductor pn junction and said electrical signal is a current signal.

30. The method of claim 20, wherein said plasmons positioned on the surface of said electrically conductive layer adjacent said dielectric layer are excited by said waveguide modes.

31. The method of claim 20, wherein said plasmons positioned on the surface of said electrically conductive layer adjacent said dielectric layer are excited by said fluorescing material.

* * * * *